United States Patent [19]

Fisher et al.

[11] Patent Number: 5,323,771
[45] Date of Patent: Jun. 28, 1994

[54] ENDOTRACHEAL TUBE INTRODUCER

[75] Inventors: Joseph A. Fisher, 113 Franmore Circle, Thornhill, Ontario, Canada, L4J 3B9; Alan Berdowski, 306 Wychwood Avenue, Toronto, Ontario, Canada, M6C 2T8

[73] Assignees: Joseph Arnold Fisher, Thornhill; Alan Berdowski, Toronto, both of Canada

[21] Appl. No.: 863,112

[22] Filed: Apr. 3, 1992

[30] Foreign Application Priority Data

Mar. 30, 1992 [CA] Canada ............... 2064396

[51] Int. Cl.$^5$ ............... A61M 16/00
[52] U.S. Cl. ............... 128/200.26; 128/207.14
[58] Field of Search ............... 128/200.26, 207.14, 128/207.15

[56] References Cited

U.S. PATENT DOCUMENTS

| | | | |
|---|---|---|---|
| 2,442,573 | 6/1948 | Stafford | 604/279 |
| 3,044,461 | 7/1962 | Murdock | 128/4 |
| 3,169,529 | 2/1965 | Koenig | 128/207.14 |
| 3,968,800 | 7/1976 | Vilasi | 128/207.14 |
| 4,068,658 | 1/1978 | Berman | 128/200.26 |
| 4,090,518 | 5/1978 | Elam | 128/207.15 |
| 4,211,234 | 7/1980 | Fisher | 128/200.26 |

FOREIGN PATENT DOCUMENTS 0150465 8/1985 European Pat. Off.
284335 9/1988 European Pat. Off.

*Primary Examiner*—Edgar S. Burr
*Assistant Examiner*—Aaron J. Lewis
*Attorney, Agent, or Firm*—Ivor M. Hughes; Neil H. Hughes

[57] ABSTRACT

An endotracheal tube introducer comprising a proximal end and a distal end, the proximal end comprising a mouth of greater diameter than an endotracheal tube being inserted into it and an elongated portion connected to, and extending longitudinally away from, the mouth for insertion thereof past the epiglottis, between the vocal cords, into the trachea, the elongated portion comprising at least one guide and reinforcing portion extending longitudinally along the length of the elongated portion away from the proximal end and mouth, and relatively thin pliable side portions or wings extending laterally from the sides of the guide portion, one from each side and overlap one another at least proximate the distal end.

23 Claims, 2 Drawing Sheets

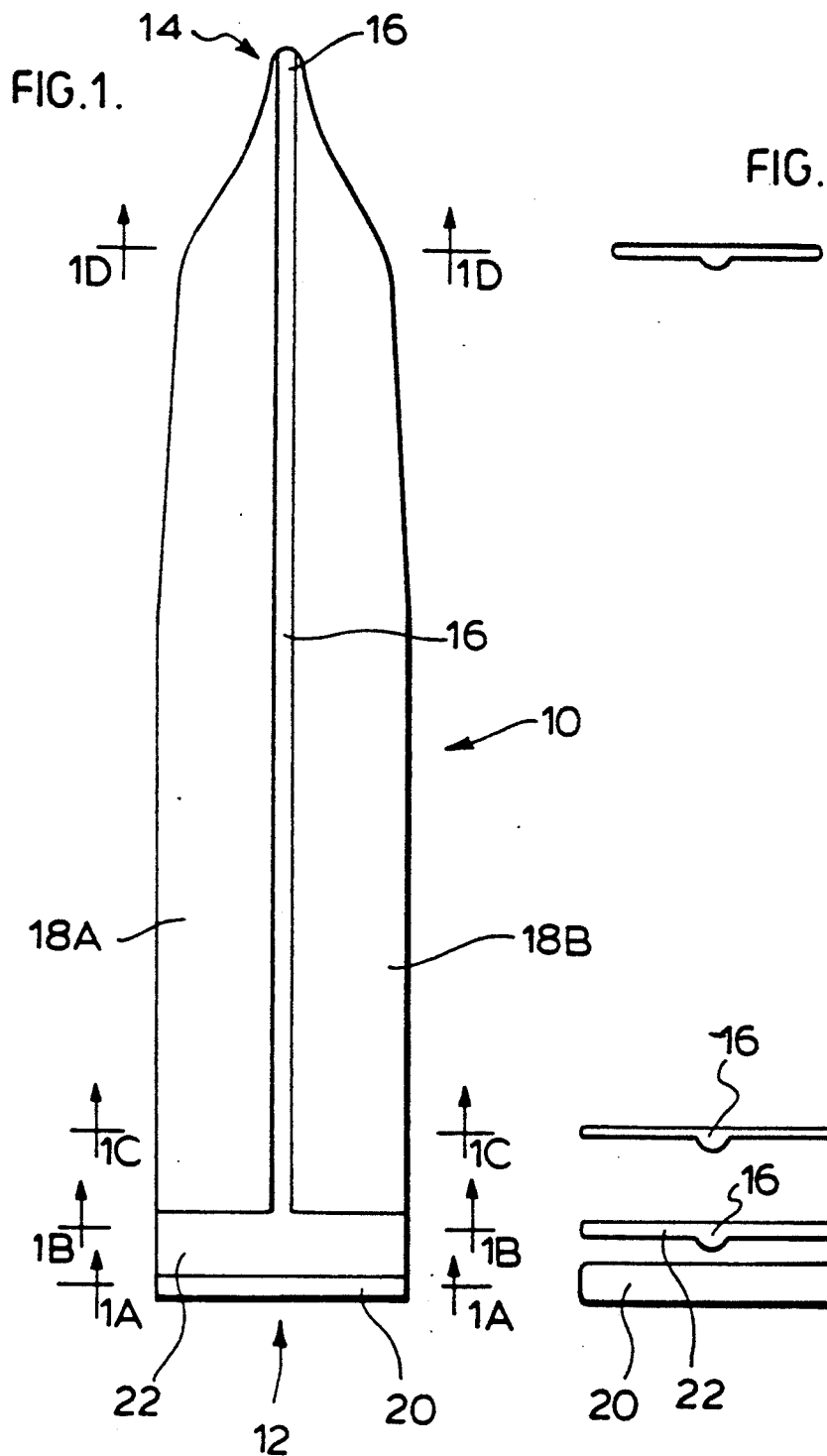

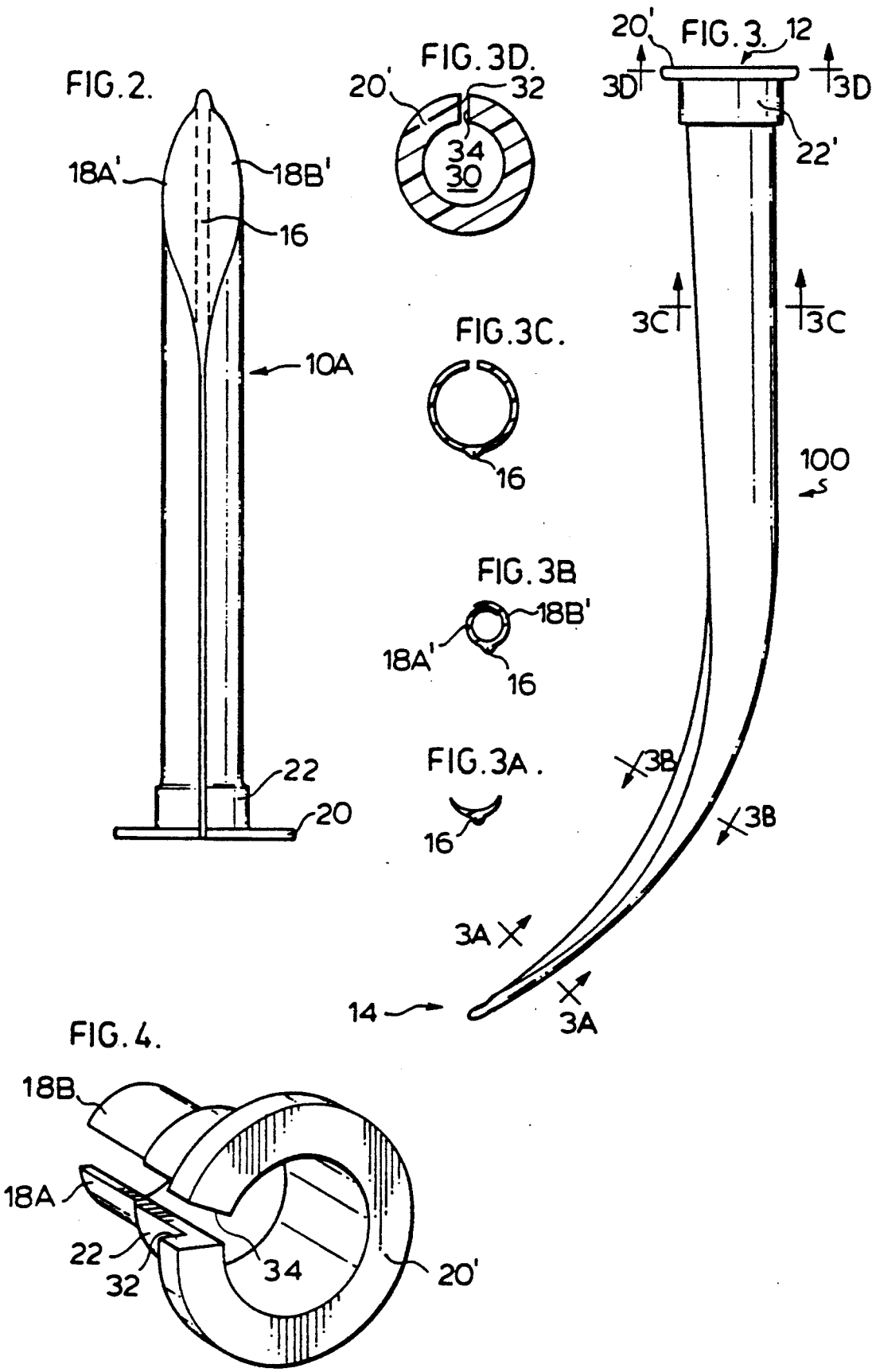

ENDOTRACHEAL TUBE INTRODUCER

FIELD OF INVENTION

This invention relates to an Improved Endotracheal Tube Introducer.

BACKGROUND OF THE INVENTION

Devices have been provided in the past for assisting to introduce the endotracheal tube past the vocal cords into the trachea. One such device was a "stylette type" introducer. The stylette introducer was of small diameter such as a wire positioned to extend between the vocal cords into the trachea. The endotracheal tube was then placed on the guide wire and advanced over the stylette past the vocal cords. In use, however, it was not always possible to pass the endotracheal tube over the stylette as the endotracheal tube introducer would from time to time get caught on various structures in the pharynx including the opening of the larynx causing trauma to these structures. Additionally, the use of the stylette required the use of two hands to manipulate the endotracheal tube over the stylette when often only one hand was available as the other hand was holding the laryngoscope.

Another proposal provided for a pharyngeal introducer which did not pass between the vocal cords, but sat in the upper pharynx and generally directing the endotracheal tube "towards" the vocal cords and larynx blindly. In use the endotracheal tube was inserted into the pharyngeal introducer and passed inside the introducer whose curvature was designed to guide the endotracheal tube towards the larynx. In use, however, this type of device had a fairly low success rate even in the hands of the most skilled and did not prevent any trauma of the advancing endotracheal tube to the tissue along its way. Furthermore, it cannot be removed when used and thus, the patients mouth continued to be propped open in an exaggerated manner dictated by the diameter of such introducers generally of large diameter.

The endotracheal tube introducer in U.S. Pat. No. 4,211,234 constituted an improvement to the previous devices and referred to a number of devices the particulars of which are incorporated herein by reference. The device in U.S. Pat. No. 4,211,234 while an advance over the prior art, because of its construction still necessitated the use of substantial material at the distal end of the device to surround the endotracheal tube when advancing along the interior of the endotracheal tube introducer. Thus, even if the amount of material at the distal end is wrapped tightly, a substantial amount of material still exists which must be passed between the vocal cords and into the larynx. If such volume of material is packed very tightly, spreading or unwrapping of the material may be difficult as the endotracheal tube is advanced along the interior of the endotracheal tube introducer.

Furthermore, the device in U.S. Pat. No. 4,211,234 is not easily manufactured because of the use of two different types of material which have to be joined and then whose diameter must be minimized by complex wrapping and compression procedures.

It is therefore an object of the invention to provide an improved endotracheal tube introducer which minimizes the amount of material and thus, minimizes the amount of material and the diameter of the material at the distal end which must pass between the vocal cords.

It is a further object of the invention to provide such a endotracheal tube introducer which is able to control the advancement of the endotracheal tube within the introducer, but employs a minimum amount of material to maintain such control.

It is still a further object of the invention to provide an endotracheal tube introducer of minimal distal cross-sectional area when packed or wrapped for use yet provides minimal resistance to unwrapping or spreading during the advancement of the endotracheal tube through the endotracheal tube introducer thereby resulting in better success rates for intubation.

It is a still further object of the invention to provide such device manufactured from one piece of material (in the preferred form) and which is more easily manufactured.

Further, and other objects of the invention will be apparent to those skilled in the art from the following Summary of the Invention, Drawings, and Detailed Description of Embodiments of the Invention shown in the drawing.

SUMMARY OF THE INVENTION

According to one aspect of the invention, an improved endotracheal tube introducer is provided, the endotracheal tube introducer comprising a proximal end and a distal end and preferably being curved along its length. The proximal end comprises a mouth of greater diameter than an endotracheal tube being inserted into it and an elongated portion connected to, and extending longitudinally away from, the mouth for insertion thereof past the epiglottis, between the vocal cords, into the trachea. The elongated portion comprises at least one guide and reinforcing portion extending longitudinally along the length of the elongated portion away from the proximal end and mouth. Relatively thin pliable side portions or wings extend laterally from the sides of the guide portion (for example one from each side), present free edges unconnected to any other portion of the endotracheal tube introducer, and which wings overlap one another at least proximate the distal end. The side portions or wings preferably taper towards the distal end and preferably each taper from the guide or reinforcing portion to its free edge so that when an endotracheal tube is to be introduced into the trachea of a patient with the assistance of the endotracheal tube introducer, the endotracheal tube is inserted into the mouth of the endotracheal tube introducer at the proximal end of the endotracheal tube introducer and the side portions or wings at least partially encircle the endotracheal tube to maintain the endotracheal tube within the volume of the endotracheal tube introducer. In one embodiment the side portions or wings overlap and taper presenting an interior volume surrounding the longitudinal axis of diminishing diameter towards the distal end. As the endotracheal tube is advanced along the length of the endotracheal tube introducer towards the distal end, the overlapping side portions are caused to unwrap, spread or expand but still engage the peripheral surface of the endotracheal tube thereby controlling the endotracheal tube within the endotracheal tube introducer and guiding the endotracheal tube past the epiglottis, between the vocal cords and into the trachea. The endotracheal tube introducer is thereafter removed by causing the side portions to be fully unwrapped, spread and separated to facilitate the quick and easy removal of the introducer from the patient's mouth leaving the endotracheal tube positioned for use in the endotracheal.

The mouth of the introducer may be surrounded by an interupted annular wall preferably carrying a radially extending handle extending circumferentially for at least a substantial portion of the circumference of the mouth around the mouth. In one embodiment the annular wall and handle are continuous for substantially 350° around the mouth terminating at an end. The handle is of such thickness so that when the edge portions of each circumferential end of the handle engage, the engagement of the ends prevents the overlap of the spaced apposing edges of the annular wall as they become squeezed during intubation.

The device is preferably manufactured from thermoplastics material for example, low density polyethelyne (or any other thermoplastic capable of being subjected to heating and cooling cycles to allow its formability) by being subjected to heating and cooling cycles to allow for its forming. The raw pelletized polyethylene material is, for example, moulded into a homogeneous sheet of material of specified thicknesses. The sheet is then wrapped around a cyindrical tube or rod after heating causing the sheet to curl to form an interrupted tube. The tube is then heated and caused to curve about a center along its longitudinal axis extending from the proximal end to the distal end such that the side portions or wings of the endotracheal tube introducer are caused to overlap and taper presenting an interior volume a diminishing diameter around the longitudinal axis towards the distal end.

Thus by using a constrictor moulding process after a typical injection moulding process the endotracheal tube introducer is formed. The Component is thus formed through as series of operations employing heating and cooling cycles throughout the sequential operation of transforming the raw pelletized material into a homogeneous controlled wall thickness rendering its tubular in form and then being curved along its longitudinal axis between the proximal and distal ends (for example by the constrictor moulding process) such that the diameter of the volume within the overlapped wings or side portions around the axis is diminished over its length towards the distal end.

In this regard the material is first injection moulded into a flat sheet, then rolled into a tubular form in the direction of its axis and then curved with the guide portion forming the convex outer surface of the endotracheal tube introducer with the opening between the side portions near the proximal end and the mouth located on the interior or concave inner surface of the curved endotracheal tube introducer. This curving causes the side portions or wings closer the distal end to overlap or wrap with one another closing the interior volume of the endotracheal tube introducer proximate the distal end.

The side portions or wings of the guide portion taper towards the distal end so that in one embodiment proximate the distal end the side portions or wings have disappeared.

In the use of the introducer, under direct laryngoscopy, the patient's mouth is opened and a laryngoscope blade is inserted into the mouth in an attempt to visualize the laryngeal structures. The introducer is grasped by the middle or distal phalanx of the second and third fingers and the tip of the thumb is placed on the proximal end of the endotracheal tube. The distal tip of the introducer is then passed into the mouth and placed between the vocal cords under direct vision or "by feel". When the proper position of the introducer is achieved, the thumb advances the endotracheal tube further into the introducer without advancing the introducer. This is affected by the second and third fingers providing counter traction on the endotracheal tube introducer and in doing so they adduct causing the circumferential edges of the handle to engage precluding and preventing the overlap of the side portions proximate the proximal end of the introducer, thereby precluding any entrapping of the endotracheal tube by the endotracheal tube introducer side portions. As the endotracheal tube advances further into the introducer, the side portions or wings are sequentially unwrapped or spread thereby unwrapping the overlapped wrapped portions of the side portions. (Because of the construction and method of manufacture of one embodiment, the overlapped portions generally, because of the tapering, provide spiral overlapped side portions or wings.)

The wings because they retain some elastic memory, continue during intubulation to at least partially surround the endotracheal tube and guide it down the center of the introducer. If the side portions did not overlap to some extent towards the distal end, the side portions may not, depending on the design of the introducer, sufficiently control the advance of the endotracheal tube to enable the endotracheal tube to follow the direction of the endotracheal tube introducer into the larynx. Thus it is important to ensure the guidelines herein be substantially followed.

When the full length of the endotracheal tube has been advanced through the introducer, the laryngoscope can be removed from the patient's mouth. The endotracheal tube is then held in place with one hand while traction is applied to the introducer causing it to separate from the endotracheal tube through the gap formed as the side portions or wings are pulled apart.

As can be appreciated, in order to give reinforcement, the spine or guide portion may be thicker than the side portions or wings. As can also be appreciated, the endotracheal tube introducer may be made from other than low density polyethelyne provided the material provides sufficient pliability and memory to permit the formation of the endotracheal tube introducer for example, by the steps of injection molding forming the injection molded portion into a tube and then curving the portion (as for example by a constrictor moulding process) for permitting delivery of the endotracheal tube to the larynx.

An embodiment of the invention will now be illustrated with reference to the following drawings of the preferred embodiment of the invention.

BRIEF DESCRIPTION OF THE DRAWINGS

FIG. 1 is a plan view of the blank obtained from an injection molding step for making the blank used in the formation of the endotracheal tube introducer.

FIGS. 1A, 1B, 1C, and 1D are cross-sectional views of the blank in FIG. 1 looking in the direction of the arrows of the lines A—A, B—B, C—C and D—D respectively.

FIG. 2 is a plan view of the blank shown in FIG. 1 formed into a tubular structure.

FIG. 3 is a side plan view of the tubular portion formed in FIG. 2 having been curved along its longitudinal axis to provide the finished endotracheal tube introducer.

FIGS. 3A, B, C and D are cross-sectional views taken along the lines 3A—3A, 3B—3B, 3C—3C and 3D—3D looking in the direction of the arrows shown in FIG. 3.

FIG. 4 is a perspective close-up view of part of the structure shown in FIG. 3.

DETAILED DESCRIPTION OF PREFERRED EMBODIMENTS OF THE INVENTION

With reference to FIG. 1, there is shown a blank 10 injection molded from low density polyethylene material (surlin thermoplastic resin) having proximal end 12 and distal end 14, a central thickened guide portion or spine 16 and side or wing portions 18A and 18B on either side of spine or guide portion 16. the side portions or wings 18A and 18B are symmetrical about guide 16. At proximal end 12 thickened portion 20 shown in cross-section in FIG. 1A is provided joined to a reinforcing portion 22 shown in cross-section in FIG. 1B joined to the wing portions 18A and 18B. As is shown in FIG. 1, the side portions 18A and 18B taper as they approach the distal end 14.

With reference to FIG. 2, blank 10 has been heated and formed into a tubular shape 10A about cylindrical rod or tube (not shown) and permitted to cool. The tubular formation of blank 10 into tubular structure 10A is accomplished by heating, by placing the heated blank on a suitable cylindrical rod or tube and thereafter permitting the formed blank to cool to take the shape shown in FIG. 2. Preferably the blank component is wrapped around a mould which is 30% larger in diameter than the inner diameter of the finished part, then immersed in heated water at 155° F. for 90 seconds and then transferred to cold water at 50° F. for 2 minutes.

The structure 10A formed in FIG. 2 is then heated and bent in such a way that portions 18A and 18B of side portions or wings 18A and 18B extending towards the distal end overlap (see FIG. 3) using the Charlton constrictor moulding process (see FIG. 3B found with FIG. 3). The bending and overlapping and thus tapering of the distal portions of the intubation device 10A are thus accomplished having the structure shown in FIG. 5. Thus, with reference to FIG. 3, the thickened flange 20 has become radially extending circumferential handle 20' substantially surrounding mouth 30 at the proximal end 12. Handle 20' extending 350° substantially surrounds mouth 30 and terminates at circumferential edges 32 and 34 (see FIG. 3D) for abutting one another when the endotracheal tube is advanced along the length of the endotracheal tube introducer 100 and the second and third fingers are providing counter traction on the endotracheal tube introducer thereby preventing overlap of the side portions (wings) 18A and 18B proximate the proximal end 12 from overlapping. Handle 20' is connected to reinforcing step portion 22' extending circumferentially below handle 20'. Portion 22' is connected to the guide portion or spine 16 and the side portions or wings 18A and 18B which extend towards the distal end 14, as is apparent for FIG. 3.

The lower portion of the endotracheal tube introducer 100 is curved with the spine or guide portion 16 being convexly curved on the outer curved portion of the introducer 100. The side portions or wings 18A and 18B close to the distal end (18A', and 18B') are concavely curved on their inner surface and overlap with one another as at 18A' and 18B' (see FIG. 3B). In the upper portions of the endotracheal tube introducer, side portions or wings 18A and 18B (see FIG. 3C) do not overlap. However as the endotracheal tube introducer tapers towards the distal end, the wings overlap. As an the endotracheal tube advances inside the endotracheal tube introducer 100 (when in use) the endotracheal tube introducer controls the direction of advancement of the endotracheal tube. Without the overlapping portions of the endotracheal tube introducer at 18A' and 18B' the endotracheal tube may veer off course and not enter the larynx.

With reference to FIG. 4, a close-up view is shown of the integral one piece construction of the portions 20, 22 and the wings 18A and 18B.

A sample blank would be 21 cm in length and 5.5 cm in width from the outer edges of the side portions 18A and 18B proximate proximal end 12. The side portions have been tapered and for the last about 2 cm of the length of the blank, the side portions 18A' and 18B' are of minimal width. Approximately 12 cm of the blank from the distal end 14 of the blank when formed into the endotracheal tube introducer 100 is curved to form an arc of generally about 71°. The handle 20' is approximately 6 mm in length and 2 mm in thickness. The side portions 18A and 18B have a thickness of 0.5 mm. and the spine 16 has a thickness of 1.0 mm. Intermediate reinforcing portion 22', has a thickness of 1.5 mm. and a length of 10.0 mm.

In use, the patient's mouth is opened and a laryngoscope blade (not shown) is inserted into the mouth of the patient attempting to visualize the laryngeal structures. The introducer 100 is grasped with the middle phalanx of the second and third fingers and the tip of the thumb (not shown) is placed on the proximal end 12 of the endotracheal tube. The distal tip (14) of the introducer (100) is then passed into the mouth and placed between the vocal cords under direct vision or "by feel". When proper position of the introducer 100 is achieved, the thumb advances the endotracheal tube further into the introducer without advancing the introducer. This is effected by the second and third fingers providing counter traction on the endotracheal tube introducer. At the same time edges 32 and 34 abut to preclude side portions 18A and 18B closer to proximal end 12 from overlapping one another which would interfere with the advancement of the endotracheal tube.

As the endotracheal tube advances further into the introducer, the spiral overlapping side portions or wings 18A' and 18B' sequentially unwrap, but continue because of their elastic memory to at least partially surround the endotracheal tube and guide it along spine 16 (the center) of the introducer 100. When the full length of the endotracheal tube is advanced through the introducer, the laryngoscope can be removed from the patient's mouth. The endotracheal tube is then held in place with one hand while traction is applied to the introducer causing it to separate from the endotracheal tube through the gap formed as the wings or side portions 18A' and 18B' and 18A and 18B are pulled apart.

As many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. An endotracheal tube introducer comprising a proximal end and a distal end, the proximal end comprising a mouth of greater diameter than an endotracheal tube being inserted into it and an elongated portion connected to, and extending longitudinally away from, the mouth for insertion thereof past the epiglottis, between the vocal cords, into the trachea, the elongated portion comprising at least one guide and reinforcing portion extending longitudinally along the length of the elongated portion away from the proximal end and mouth, and relatively thin pliable side portions or wings extending laterally from the sides of the guide portion, one from each side, and presenting free edges unconnected to any other portion of the endotracheal tube introducer and which side portions or wings overlap one another at least proximate the distal end.

2. The endotracheal tube introducer of claim 1 wherein the endotracheal tube introducer is curved along its length.

3. The introducer of claim 2 wherein the mouth of the introducer is surrounded by an interupted annular wall carrying a radially extending handle extending circumferentially for at least a substantial portion of the circumference of the mouth, around the mouth.

4. The introducer of claim 3 wherein the mouth of the introducer is surrounded by an interrupted annular wall carrying a radially extending handle extending circumferentially for at least a substantial portion of the circumference of the mouth, around the mouth and the annular wall and handle are continuous for substantially 350° around the mouth terminating at an end.

5. The introducer of claim 4 wherein the handle is of such thickness so that when the edge portions of each circumferential end of the handle engage, the engagement of the ends prevents the overlap of the spaced apposing edges of the annular wall when they are squeezed together during intubation.

6. The improved introducer of claim 1 wherein the side portions or wings taper towards the distal end.

7. The introducer of claim 6 wherein the mouth of the introducer is surrounded by an interupted annular wall carrying a radially extending handle extending circumferentially for at least a substantial portion of the circumference of the mouth, around the mouth.

8. The introducer of claim 7 wherein the mouth of the introducer is surrounded by an interrupted annular wall carrying a radially extending handle extending circumferentially for at least a substantial portion of the circumference of the mouth, around the mouth and the annular wall and handle are continuous for substantially 350° around the mouth terminating at an end.

9. The introducer of claim 8 wherein the handle is of such thickness so that when the edge portions of each circumferential end of the handle engage, the engagement of the ends prevents the overlap of the spaced apposing edges of the annular wall when they are squeezed together during intubation.

10. The endotracheal tube of claim 6 wherein the side portions or wings overlap and taper presenting an interior volume surrounding the longitudinal axis of diminishing diameter towards the distal end.

11. The introducer of claim 10 wherein the mouth of the introducer is surrounded by an interupted annular wall carrying a radially extending handle extending circumferentially for at least a substantial portion of the circumference of the mouth, around the mouth.

12. The introducer of claim 11 wherein the mouth of the introducer is surrounded by an interupted annular wall carrying a radially extending handle extending circumferentially for at least a substantial portion of the circumference of the mouth, around the mouth and the annular wall and handle are continuous for substantially 350° around the mouth terminating at an end.

13. The introducer of claim 12 wherein the handle is of such thickness so that when the edge portions of each circumferential end of the handle engage, the engagement of the ends prevents the overlap of the spaced apposing edges of the annular wall when they are squeezed together during intubation.

14. The introducer of claim 1 wherein the thin pliable side portions or wings each taper from the guide or reinforcing portion to its free edge.

15. The introducer of claim 14 wherein the side portions or wings of the guide portion taper towards the distal end so that proximate the distal end the side portions or wings have disappeared.

16. The introducer of claim 14 wherein the mouth of the introducer is surrounded by an interrupted annular wall carrying a radially extending handle extending circumferentially for at least a substantial portion of the circumference of the mouth, around the mouth and the annular wall and handle are continuous for substantially 350° around the mouth terminating at an end.

17. The introducer of claim 16 wherein the handle is of such thickness so that when the edge portions of each circumferential end of the handle engage, the engagement of the ends prevents the overlap of the spaced apposing edges of the annular wall when they are squeezed together during intubation.

18. The introducer of claim 1, 2 or 6 wherein the introducer comprises a thermoplastic material.

19. The introducer of claim 4, 8 or 12 wherein the introducer comprises a thermoplastic material.

20. The introducer of claim 17, 5 or 9 wherein the introducer comprises a thermoplastic material.

21. The introducer of claim 13 or 15 wherein the introducer comprises a thermoplastic material.

22. The introducer of claim 10, 14 or 3 wherein the introducer comprises a thermoplastic material.

23. The introducer of claim 7, 11 or 16 wherein the introducer comprises a thermoplastic material.

* * * * *

UNITED STATES PATENT AND TRADEMARK OFFICE
CERTIFICATE OF CORRECTION

PATENT NO. : 5,323,771
DATED : June 28, 1994
INVENTOR(S) : Joseph A. Fisher and Alan Berdowski It is certified that error appears in the above-identified patent and that said Letters Patent is hereby corrected as shown below:

Col. 6, line 1 should read as follows:

1. An endotracheal tube introducer comprising a proximal end and a distal end, the proximal end comprising a mouth of greater diameter than an endotracheal tube being inserted into it and an elongated portion connected to, and extending longitudinally away from, the mouth for insertion thereof past the epiglottis, between the vocal cords, into the trachea, the elongated portion comprising at least one guide and reinforcing portion extending longitudinally along the length of the elongated portion away from the proximal end and mouth, and relatively thin pliable side portions or wings connected to the guide and extending laterally from the sides of the guide portion, one from each side, and being unconnected to each other or any other structure and presenting free edges unconnected to any other portion of the endotracheal tube introducer except the guide and reinforcing portion and which side portions or wings overlap one another at least proximate the distal end.

UNITED STATES PATENT AND TRADEMARK OFFICE
CERTIFICATE OF CORRECTION

PATENT NO. : 5,323,771
DATED : June 28, 1994
INVENTOR(S) : Joseph A. Fisher and Alan Berdowski It is certified that error appears in the above-identified patent and that said Letters Patent is hereby corrected as shown below:

Column 8, Claim 14 should read as follows:

14. The introducer of claim 1 wherein the thin pliable side portions or wings which side portions or wings each tapers towards its free edge.

Signed and Sealed this

Tenth Day of October, 1995

*Attest:*

BRUCE LEHMAN

*Attesting Officer*  Commissioner of Patents and Trademarks